United States Patent
Burton

(10) Patent No.: US 9,084,875 B2
(45) Date of Patent: Jul. 21, 2015

(54) SINGLE PIECE DOUBLE WALL DILATION BALLOON CATHETER

(71) Applicant: Cook Incorporated, Bloomington, IN (US)

(72) Inventor: David G. Burton, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 13/859,479

(22) Filed: Apr. 9, 2013

(65) Prior Publication Data
US 2013/0282097 A1   Oct. 24, 2013

Related U.S. Application Data

(63) Continuation of application No. 12/508,951, filed on Jul. 24, 2009, now abandoned.

(60) Provisional application No. 61/089,746, filed on Aug. 18, 2008.

(51) Int. Cl.
*B29C 49/04* (2006.01)
*A61M 25/10* (2013.01)
*A61F 2/958* (2013.01)

(52) U.S. Cl.
CPC ............ *A61M 25/104* (2013.01); *A61F 2/958* (2013.01); *A61M 25/1011* (2013.01); *A61M 25/1029* (2013.01); *A61M 2025/1013* (2013.01); *A61M 2025/1072* (2013.01); *A61M 2025/1075* (2013.01); *A61M 2025/1088* (2013.01)

(58) Field of Classification Search
None
See application file for complete search history.

(56) References Cited

U.S. PATENT DOCUMENTS

| | | |
|---|---|---|
| 4,490,421 A | 12/1984 | Levy |
| RE32,983 E | 7/1989 | Levy |
| 4,909,252 A | 3/1990 | Goldberger |
| RE33,561 E | 3/1991 | Levy |
| 5,087,394 A | 2/1992 | Keith |
| 5,264,260 A | 11/1993 | Saab |
| 5,342,301 A | 8/1994 | Saab |
| 5,423,754 A | 6/1995 | Cornelius et al. |
| 5,512,051 A | 4/1996 | Wang |

(Continued)

FOREIGN PATENT DOCUMENTS

| | | |
|---|---|---|
| EP | 0135990 | 9/1990 |
| WO | WO 2007/075585 A2 | 7/2007 |

*Primary Examiner* — Monica Huson
(74) *Attorney, Agent, or Firm* — Brinks Gilson & Lione

(57) ABSTRACT

The present invention relates to medical devices for dilating or enlarging strictures or narrowed regions of body vessels. Specifically, the present invention relates to a high pressure dilation balloon catheter that includes an elongate shaft extending between a proximal end and a distal end, the proximal end being adapted for attachment to a source of inflation fluid, and a lumen extending through the shaft adapted for the passage of the inflation fluid; and a balloon disposed on the distal end of the shaft and having a balloon body extending between a proximal end and a distal end of the balloon. The balloon body includes a first layer, a second layer disposed about at least a portion of the first layer, a plurality of longitudinally extending rib members disposed between the first and the second layers and configured to form a plurality of sealed cavities between the first and the second layers; and a balloon chamber within the first layer, the balloon chamber being in a communication with the lumen of the shaft for inflating and deflating the balloon.

21 Claims, 6 Drawing Sheets

(56) References Cited

U.S. PATENT DOCUMENTS

| | | | |
|---|---|---|---|
| 5,554,119 A | 9/1996 | Harrison et al. | |
| 5,746,762 A | 5/1998 | Bass | |
| 5,755,690 A | 5/1998 | Saab | |
| 5,792,105 A | 8/1998 | Lin et al. | |
| 5,913,813 A | 6/1999 | Williams | |
| 6,491,712 B1 | 12/2002 | O'Connor | |
| 6,592,550 B1 * | 7/2003 | Boatman et al. | 604/103.06 |
| 6,629,952 B1 | 10/2003 | Chien et al. | |
| 6,712,833 B1 | 3/2004 | Lee et al. | |
| 6,936,057 B1 | 8/2005 | Nobles | |
| 7,942,847 B2 | 5/2011 | Stupecky et al. | |
| 2004/0015052 A1 | 1/2004 | Barthel | |
| 2004/0215315 A1 | 10/2004 | Jones et al. | |
| 2005/0167888 A1 | 8/2005 | Owens et al. | |
| 2005/0177130 A1 | 8/2005 | Konstantino et al. | |
| 2006/0052813 A1 | 3/2006 | Nobles | |
| 2006/0058830 A1 | 3/2006 | Hermann et al. | |
| 2006/0122642 A1 | 6/2006 | Steadham et al. | |
| 2006/0135982 A1 | 6/2006 | Simpson | |
| 2006/0184111 A1 | 8/2006 | Lim et al. | |
| 2006/0293750 A1 | 12/2006 | Sherman et al. | |
| 2007/0067010 A1 | 3/2007 | Wang et al. | |
| 2007/0118076 A1 | 5/2007 | Lim et al. | |
| 2007/0167973 A1 | 7/2007 | Stupecky et al. | |
| 2007/0185443 A1 | 8/2007 | Euteneuer et al. | |
| 2007/0185457 A1 | 8/2007 | Euteneuer et al. | |
| 2008/0078405 A1 * | 4/2008 | Crumback et al. | 128/207.15 |

\* cited by examiner

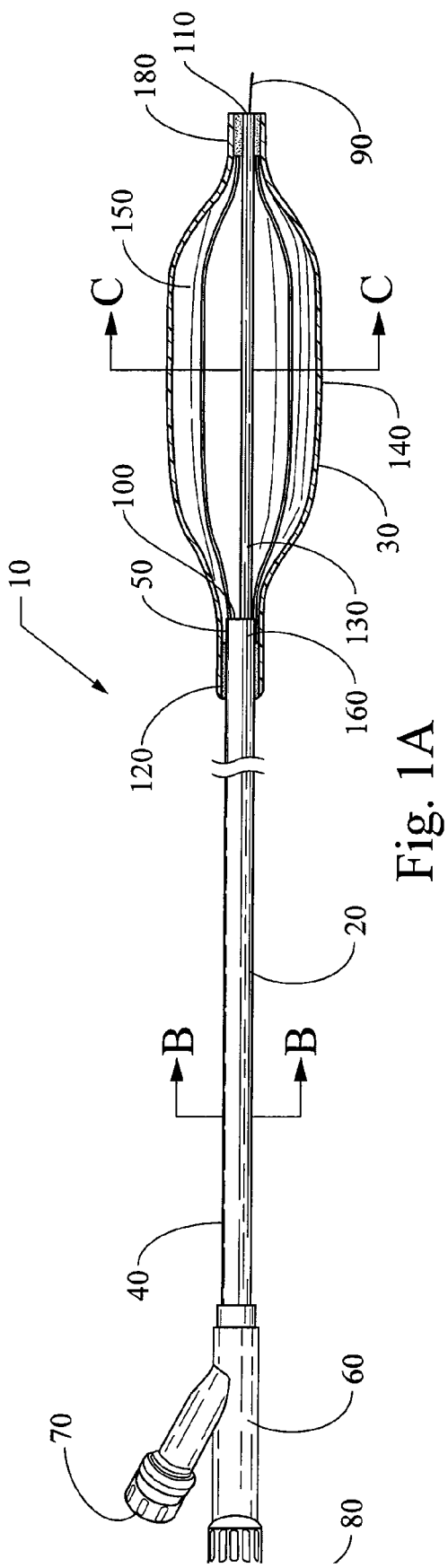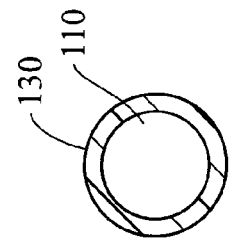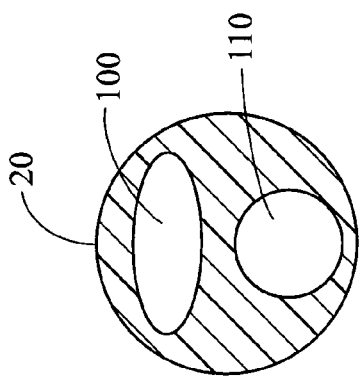

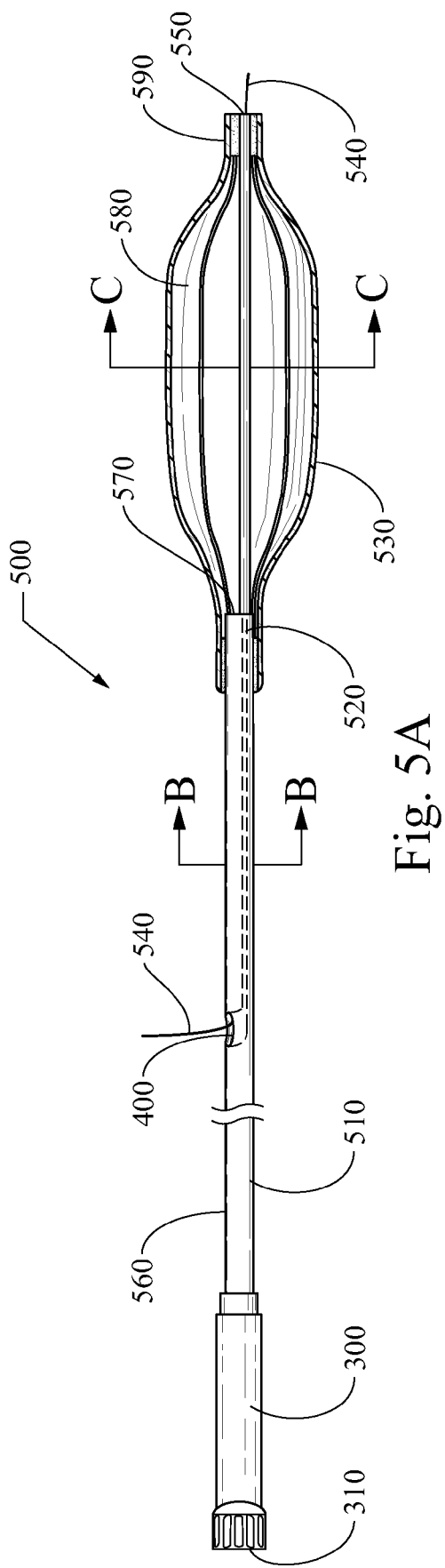
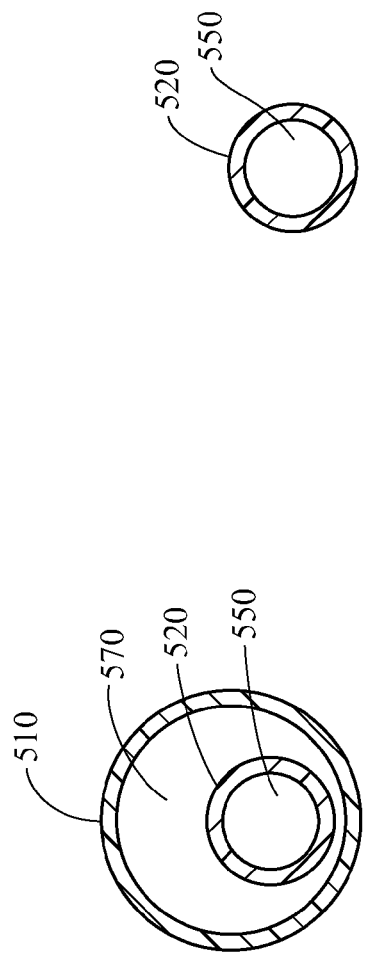
Fig. 5A
Fig. 5B
Fig. 5C

SINGLE PIECE DOUBLE WALL DILATION BALLOON CATHETER

RELATED APPLICATIONS

The present patent document is a Continuation Application of U.S. patent application Ser. No. 12/508,951, filed Jul. 24, 2009, which claims the benefit of the filing date under 35 U.S.C. §119(e) of Provisional U.S. Patent Application Ser. No. 61/089,746, filed Aug. 18, 2008, which are hereby incorporated by reference.

BACKGROUND

A variety of body lumens are subject to undesired strictures or narrow regions. For example, blood vessels can be blocked or narrowed by atherosclerosis, while esophageal strictures can arise from individual anatomical differences, or from diseases such as connective tissue disorder.

Procedures for dilating or enlarging such strictures or narrowed regions often entail the use of a balloon dilation catheter. In general, such catheters include a deflated balloon which can be positioned across a particular stricture or narrowed region, and which is then inflated with an inflation fluid in order to widen the lumen without trauma to the wall of the lumen.

Conventional dilation balloons fall into high, medium, and low pressure ranges. Low pressure balloons are those that have burst pressures below 6 atmospheres (ATM) ($6.1 \times 10^5$ Pascals). Medium pressure balloons are those that have burst pressures between 6 and 15 ATM ($6.1 \times 10^5$ and $1.2 \times 10^6$ Pa). High pressure balloons are those that have burst pressures above 15 ATM ($1.2 \times 10^6$ Pa) and as high as 30 ATM. The term "burst pressure" refers to the maximum pressure which can be slowly applied to the balloon (at a specific temperature and for a specified amount of time (e.g., seconds or minutes)) without causing it to rupture or burst. Burst pressure is determined by such factors as the wall thickness and tensile strength of the balloon material.

High pressure balloons are desirable because they have the ability to exert more force and "crack" hard lesions. High pressure balloons are useful in high pressure procedures, such as Percutaneous Transluminal Angioplasty (PTA) in the peripheral vasculature, including the iliac, femoral, iliofemoral, popliteal and renal arteries, and for the treatment of obstructive lesions of native or synthetic arteriovenous dialysis fistulae. High pressure balloons are also useful in stent deployment.

A biocompatible metal stents are often used to prop open blocked coronary arteries and to keep them from re-closing after balloon angioplasty. In an exemplary procedure, balloon of appropriate size and pressure is first used to open the lesion. The process is then repeated with a stent crimped onto a high pressure balloon. The stent is deployed when the balloon is inflated. A medium to high pressure balloon is preferable for stent deployment because the stent must be forced against the artery's interior wall so that it will fully expand, thereby precluding the ends of the stent from projecting into the arterial channel, which may inhibit flow there through and encourage the formation of thrombus.

High pressure balloon materials are typically stiffer than conventional medium or low pressure balloon materials. Whereas medium or low pressure balloons use materials such as polyethylene, high pressure balloons use materials such as Nylon 12 or PET. See, for example, U.S. Pat. No. 4,490,421, U.S. Pat. No. Re. 32,983, U.S. Pat. No. Re. 33,561, and EP 0135990, which are incorporated herein by reference in their entirety, which disclose a high molecular weight, biaxially oriented, flexible, polymeric balloon with a tensile strength of at least 31,714 psi (218.86 MPa), which can be made of PET. See, also, U.S. Pat. No. 5,264,260, which discloses a PET balloon, optionally melt blended or mixed with other polymeric or nonpolymeric materials, having an intrinsic viscosity of less than or equal to 0.6 dl/g and a calculated radial tensile strength greater than about 25,000 psi (172 MPa), and is also incorporated by reference in its entirety.

In general, improvements have been made to conventional high pressure balloons over the years. However, because these balloons are subject to the application of high pressure, these balloons are still prone to puncture or tearing, such as circular tearing of the balloons under burst pressure. Moreover, when these balloons burst in a constricted state, they often tear along a circumferential path that may lead to separation of the balloon into two or more pieces. As a consequence, forceps or other device may need to be inserted into a patient to remove the balloon pieces thus requiring more complicated and/or longer procedures.

As such, there still exists a need in the industry for high pressure balloons which display improved puncture and tearing resistance, when compared to the conventional high pressure balloons, while maintaining sufficient burst strength.

SUMMARY

In one embodiment, the invention relates to a dilation balloon catheter. The dilation balloon catheter includes an elongate shaft extending between a proximal end and a distal end, the proximal end being adapted for attachment to a source of inflation fluid, and a lumen extending through the shaft adapted for the passage of the inflation fluid; and a balloon disposed on the distal end of the shaft and having a balloon body extending between a proximal end and a distal end of the balloon. The balloon body includes a first layer, a second layer disposed about at least a portion of the first layer, a plurality of longitudinally extending rib members disposed between the first and the second layers and configured to form a plurality of sealed cavities between the first and the second layers, and a balloon chamber within the first layer, the balloon chamber being in a communication with the lumen of the shaft for inflating and deflating the balloon. The first layer, the second layer and the rib members may each be formed from a single piece of a non-porous elastomeric material, such as Nylon (Nylon 12), polyether block amide (PEBAX), PEBAX 4033, PEBAX 5533, PEBAX 6333, and poly(ethylene terephthalate) (PET).

The balloon may have an inflated diameter anywhere in the range of from about 2 millimeters to about 30 millimeters, and a length anywhere in the range of from about 2 centimeters to about 25 centimeters. The first layer may have a thickness from about 0.014 m millimeters to about 0.060 millimeters. The second layer may have a thickness from about 0.008 millimeters to about 0.047 millimeters. The proximal and the distal ends of the balloon body may each be tapered. The balloon body may include from 2 to 5 rib members circumferentially disposed about the first layer of the balloon body. The rib members may longitudinally extend though the entire length of the balloon body. The dilation balloon catheter also may include a lubricant disposed in each of the cavities. The lubricant may be silicone.

In certain embodiments, the first and the second layers may comprise different materials. The first and the second layers may also comprise different thicknesses. The balloon may be configured to exert an outward pressure of from about 12 atmospheres to about 30 atmospheres when inflated.

The shaft of the dilation balloon catheter may further include a wireguide lumen extending through at least a portion thereof. The wireguide lumen may be disposed adjacent to the inflation lumen of the shaft. The wireguide lumen may extend through a substantial portion of the shaft and terminate in a proximal port near the proximal end of the shaft. The shaft may include a port through a side wall thereof in communication with the wireguide lumen, the port being located proximal of the balloon and a substantial distance from the proximal end of the shaft. The shaft may include either one or both of these proximal ports. The wireguide lumen may include a wire guide coaxially and moveably disposed there through.

The rib members may have height from about 0.03 millimeters to about 0.50 millimeters. The rib members may comprise various cross-sectional profiles or shapes. For example, the rib members may have a non-uniform width, such as the rib members include a substantially larger width in the middle (bulging in the middle), a substantially larger width towards the second layer, or tapered width towards the first layer. Alternatively, the rib members may have a uniform width, such as, a uniform width of a single dimension.

In another embodiment, the invention relates to a method for dilating a vessel stricture by providing a dilation balloon catheter as described above; positioning the balloon within or near the vessel stricture; and inflating the balloon to dilate or widen the vessel stricture.

In yet another embodiment, the method may further include the steps of providing a stent; compressing the stent about the balloon when the balloon is in an uninflated state; and expanding the balloon to expand and deploy the stent.

BRIEF DESCRIPTION OF THE DRAWINGS

The devices, systems and methods may be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 1A-1C depict exemplary dilation balloon catheter device;

FIGS. 5A-5C depicts coaxial configuration of the shaft of an exemplary dilation balloon catheter device;

DETAILED DESCRIPTION OF THE DRAWINGS AND THE PRESENTLY PREFERRED EMBODIMENTS

Figure 2:
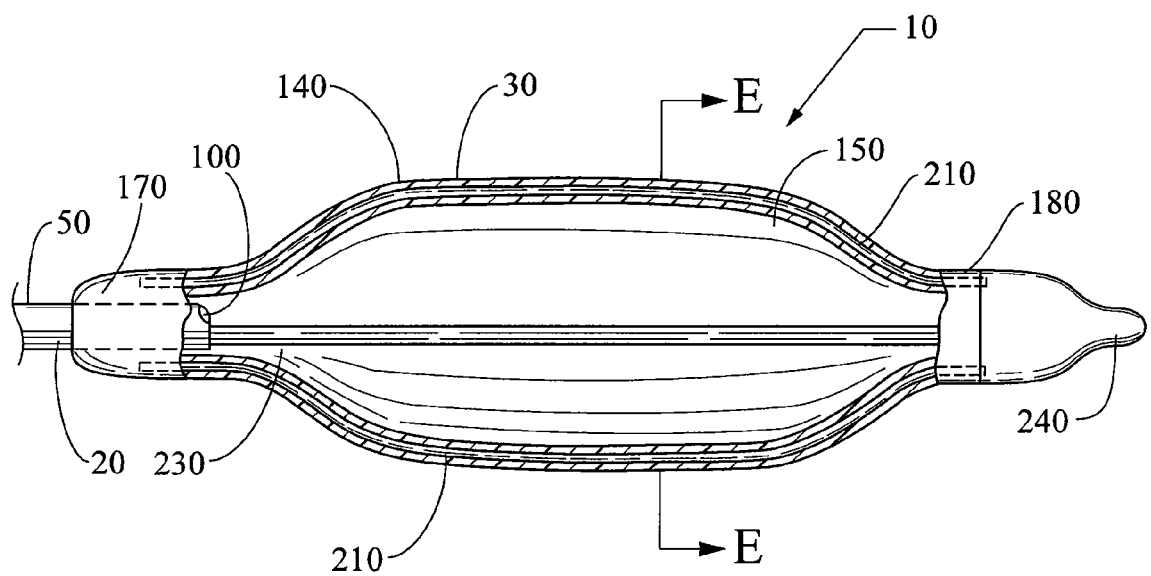
FIG. 2 depicts dilation balloon portion of the device of FIGS. 1A-1C.

The present invention relates to medical devices, and more specifically to dilation catheter devices, which can be used for dilation (i.e., mechanical widening) of strictures, during high pressure procedures, such as Percutaneous Transluminal Angioplasty (PTA) in the peripheral vasculature, including the iliac, femoral, ilio-femoral, popliteal and renal arteries, and for the treatment of obstructive lesions of native or synthetic arteriovenous dialysis fistulae. The device of the present invention can also be used for post-dilation of balloon expandable and self-expanding stents in the peripheral vasculature and other bodily lumens of a mammalian patient.

Embodiments of the dilation catheter devices described herein generally include a shaft adapted for the passage of the inflation fluid there though and a balloon disposed on the distal end of the shaft. The balloon has a balloon body that includes two separate layers (inner and outer balloon walls) and a plurality of longitudinally extending rib members disposed between the two layers and configured to form a plurality of sealed cavities between the layers.

It is believed that the inclusion of rib members within the double-walled balloon portion (i.e., balloon body) of the dilation balloon catheter device provides a balloon catheter suitable for use in high pressure applications. This is because the ribs will tend to direct any tearing along longitudinal pathway and because the rib members advantageously allow the two layers of the balloon body to expand independently of each other during inflation of the balloon, while maintaining contact with each other. Because the layers are in contact with each other during inflation but moving independently, the overall burst will be significantly higher than a single layer balloon having dimensions (e.g., thickness) equivalent to the dimensions of the two layers of the balloon body combined. In addition, the rib members function to resist circular tearing of the balloon under burst pressure.

DEFINITIONS

Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, $27^{th}$ edition.

The terms "about" or "substantially" used with reference to a quantity includes variations in the recited quantity that are equivalent to the quantity recited, such as an amount that is insubstantially different from a recited quantity for an intended purpose or function.

The terms "adapted for" or "configured to" while referring to an element of the dilation balloon catheter described herein mean that the element is changed, modified, or specifically designed so that it is suitable to perform a specified or desired function.

As used herein, "disposed" means placed or arranged in a particular order to define the relationship between elements or components of a device. The term "disposed" can include, without being limited to, terms, such as, placed, arranged, distributed, or incorporated.

The term "non-compliant" refers to a type of material that is used to form the balloon portion of the balloon catheter described herein. "Non-compliant" material may be characterized by high stiffness, rigidity, low compliance, and/or low elasticity. The term "non-compliant," throughout the instant specification, also refers to a material, which are substantially non-compliant (i.e., semi-compliant) or substantially non-elastic. These terms may be used interchangeably.

The term "proximal" refers to an area nearer to a point of reference such as an origin or a point of attachment. In this application the term proximal refers to an area nearer to the physician.

The term "distal" refers to an area further from a point of reference, e.g., further from a physician.

The term "shaft" refers to a tubular structure, such as, for example, a catheter.

The term "tubular" refers to the general shape of a device or an element of the device, which allows the device to carry fluid along a distance or fit within a tubular structure such as an artery.

The term "stent" refers to any device or structure that adds rigidity, expansion force or support to a tubular structure, such as vessel wall.

The term "stent graft" refers to a type of endoluminal prosthesis made of a tubular graft material and supported by at least one stent.

Referring to FIGS. 1A-1C, an exemplary embodiment of the present invention is shown and illustrates a high pressure dilation balloon catheter 10, which includes an elongate shaft 20 and a balloon 30 disposed on a distal end 50 of the shaft 20. As shown in the drawings, the balloon 30 comprises in its fully inflated profile shape, a cylindrical working portion with an inflated diameter located between a pair of conical end portions, and proximal and distal legs (sometimes referred to as neck portions) extending from the conical portions and affixed to the shaft. The balloon in its deflated profile shape may have several pleats (not shown) that allow the balloon to be wrapped around the shaft to reduce its profile so as to facilitate advancement of the balloon catheter into the patient.

Figure 6:
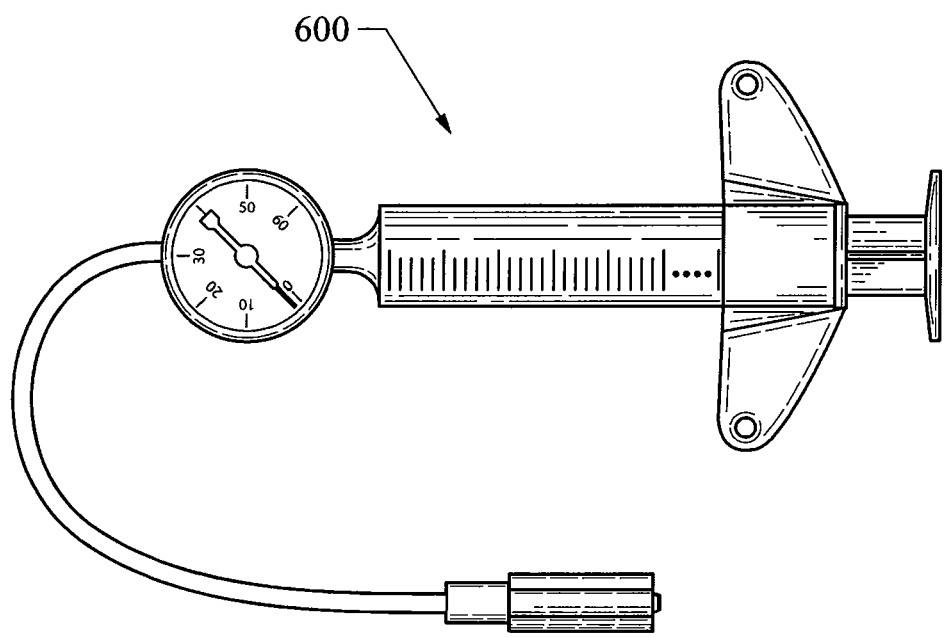
FIG. 6 depicts exemplary inflation device.

Specifically, the balloon catheter 10 includes an elongate shaft (i.e., tube) 20, which can be made from a flexible catheter tubing, such as Nylon. The shaft 20 is preferably tubular and extends between a proximal end 40 and a distal end 50, where the proximal end 40 can attach to a hub 60, which can include an inflation port 70, which then connects to a source of inflation fluid, i.e., inflation device (not shown). An exemplary inflation device, such as a syringe 600, is illustrated in FIG. 6.

As shown in FIG. 1A, the balloon catheter may be also adapted for use with optional ancillary instrumentation, such as a wire guide 90, where the hub 60 also includes a wireguide port 80 in communication with a wire guide lumen 110.

In a first illustrative embodiment, the wire-guided dilation balloon catheter 10 includes a shaft 20 that comprises a dual lumen shaft, best seen in FIG. 1B, which is a cross-section though B-B in FIG. 1A. In particular, the shaft 20 includes an inflation lumen 100 for the passage of the inflation fluid, and a wireguide lumen 110 to accommodate wire guide 90 that may be used in a procedure. The inflation lumen 100 terminates at the location near the proximal balloon bond 120 and is in fluid communication with the interior of the balloon for the delivery of the inflation fluid into the balloon 30. A single lumen shaft 130 extends from the main shaft 20 and through the balloon body 140 (FIGS. 1A and 1C) and is in communication with the wireguide lumen 110 of the shaft 20. FIG. 1C is a cross-section taken along line C-C of FIG. 1A. The shaft 130 terminates near the distal end 180 of the balloon 30 and can include a passageway via which the wire guide 90 may enter and exit the balloon catheter 10 to aid in cannulation or perform some other function. The inflation fluid, such as water or saline, for inflation of the balloon 30 is supplied via the main shaft 20 through the inflation lumen 100 and into the balloon chamber 150. The single lumen shaft 130 may be heat bonded to the distal end 160 of the shaft 20 or may be formed as a unitary structure.

As mentioned above, the dilation balloon catheter 10 of this invention includes a balloon 30 disposed on a distal end 50 of the shaft 20. The illustrative balloon 30 of the balloon catheter 10 is shown in greater detail in FIGS. 2 and 3. The balloon 30 has a balloon body 140 extending between a proximal end 170 and a distal end 180 of the balloon 30. The balloon body 140 includes a first layer (i.e., inner wall) 190 and a second layer (i.e., outer wall) 200 which is disposed about at least a portion of the first layer 190. The balloon body 140 also includes a plurality of longitudinally extending rib members 210 disposed between the first and the second layers 190, 200, and a balloon chamber 150 within the first layer 190. The balloon chamber 150 remains in communication with the inflation lumen 100 of the shaft 20 for inflating and deflating the balloon 30. As illustrated in FIG. 3, which is a cross-section though E-E of FIG. 2, the rib members 210 can form a plurality of sealed cavities 220 between the first 190 and the second 200 layers of the balloon 30.

Each of the layers 190, 200 making up the balloon 30 can be formed to have a specific inflated diameter. Preferably, the inflated diameter of the inner layer is slightly smaller than the inflated diameter of the outer layer.

The balloon portion 30 of the dilation balloon catheter 10 can be formed of a balloon material that is preferably substantially non-compliant and non-porous, and stretches a relatively small amount under pressures of 15 atmospheres or more. Various materials may be used, including Nylon (e.g., Nylon 12), polymeric materials such as poly(ethylene terephthalate) (PET), PEEK, PEBAX material, or a block copolymer thereof. Other suitable materials may also be used.

The balloon 30 can preferably be formed from a single piece of suitable balloon material by a well-known means, such as blow molding, whereby a length of PET tubing, sufficient in length to form the final desired length of the balloon, is placed and clamped within a mold conforming to the final shape of the fully distended balloon. Hot air is passed through the tubing, causing the tubing to expand against the contours of the mold. The tubing and molding process parameters necessary to achieve the desired balloon are determined by the required burst strength and recommended pressure of the balloon, the material used, and the size of the balloon. One source of the balloon portion of the illustrative embodiment is Advanced Polymers, Inc. (Salem, N.H.).

The balloon 30 can be attached to the shaft 20 by variety of methods, including by inserting the distal end 50 of the shaft 20 into the proximal opening 230 of the balloon 30 and bonding thereto using a well-known method, such as for example an ultraviolet-curable adhesive. Alternatively, the balloon 30 may be attached to the shaft 20 with the use of a solvent or by gluing. Other suitable methods of attachment are also contemplated.

Referring back to FIG. 2, the distal end 180 of the balloon 30 may have a standard tapered or domed configuration with a flexible tip 240. Alternatively, the distal end 180 of the balloon 30 may be formed so that it is generally truncate in shape, having a substantially flat end, rather than comprising standard configurations discussed above.

The balloon 30 is configured to be inflated to a predetermined or specific "inflated balloon diameter" or "outer balloon diameter." The terms "inflated balloon diameter" or "outer balloon diameter" of the balloon 30 refer to the diameter of the outer most layer of the second layer and are specific or predetermined for a given balloon. Preferably, the inflated balloon diameter can fall within a range from about 2 millimeters to about 30 millimeters depending on the application of the balloon catheter and/or the medical procedure. More preferably, the inflated balloon diameter can fall within a range from about 3 millimeters to about 14 millimeters.

Also, although the above described balloon 30 may be configured to be inflated to a single predetermined or specific balloon diameter, due to variations in pressure, materials, environmental and other factors, the inflated balloon diameter may be slightly larger or slightly smaller than the single predetermined or specific diameter of the balloon 30. For example, for a balloon configured to have the single predetermined or specific inflated balloon diameter of 10 millimeters, the balloon is configured to be inflated to an inflated balloon diameter in the range from about 9.8 millimeters to about 10.2 millimeters.

Moreover, although, in the embodiments of the device described above, the balloon 30 can have a single predetermined inflated balloon diameter, the balloon 30 can be configured to be inflated to a plurality of predetermined or specific balloon diameters, each inflated balloon diameter being the result the pressure or the amount of inflation fluid delivered to the balloon 30.

The length of the balloon body 140 can be in a range of from about 2 centimeters to about 25 centimeters; preferably the length of the balloon body 140 can be in the range from about 2 centimeters to 14 centimeters.

The balloon will preferably have a burst pressure of at least 12 ATM; and more preferably at least 20 ATM; and most preferably as high as 30 ATM.

Figure 3:
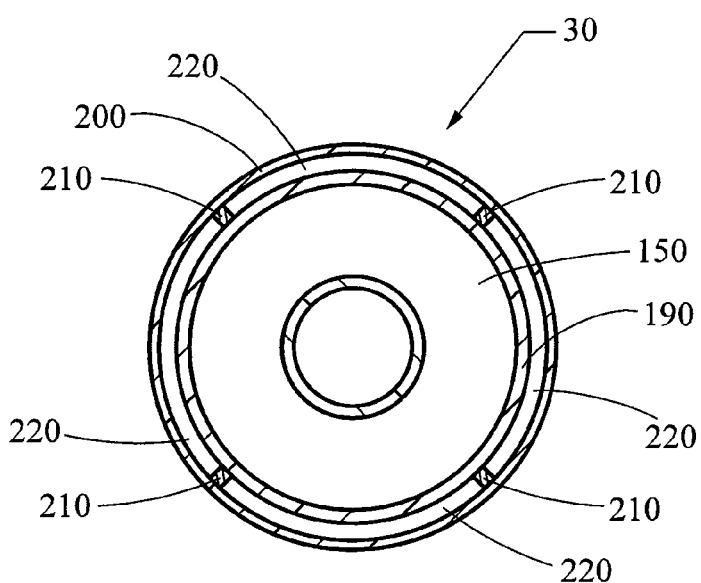
FIG. 3 shows cross-sectional view though E-E of the exemplary dilation balloon of FIG. 2.

Referring to FIG. 3, which is a cross-sectional view though E-E of the balloon catheter shown in FIG. 2, the balloon body 140 of the balloon catheter 10 includes a first layer 190 and a second layer 200, which is disposed about at least a portion of the first layer 190. The two layers 190, 200 are preferably made from a single piece of a non-porous balloon material as described above with reference to the material that may be used to form the balloon 30.

The thickness of the first (i.e., inner) layer 190 of the balloon 30 may be in a range of from about 0.014 millimeters to about 0.060 millimeters; and preferably in a range of from about 0.020 millimeters to about 0.045 millimeters. The thickness of the second (i.e., outer) layer 200 of the balloon 30 may be in a range of from 0.008 millimeters to about 0.047 millimeters; and preferably, in a range of from about 0.012 millimeters to about 0.035 millimeters.

The combined thickness of the two layers 190, 200 of the balloon body 140 will depend on the balloon size and application for which the balloon is intended. Nonetheless, it is preferred that the first layer 190 is thicker that the second layer 200 of the balloon body 140. The combined thickness of the balloon body layers 190, 200 may be in a range of from about 0.032 millimeters to about 0.08 millimeters (not taking into account the thickness of the cavity 220 between the two layers 190, 200, as discussed below). Preferably, the combined thickness of the balloon body layers 190, 200 may be in a range of from about 0.032 millimeters to about 0.07 millimeters; more preferably the combined thickness of the balloon body layers 190, 200 may be in a range of from about 0.032 millimeters to about 0.06 millimeters; and most preferably the combined thickness of the balloon body layers 190, 200 may be in a range of from about 0.032 millimeters to about 0.05 millimeters.

The balloon 30 also includes a balloon chamber 150 within the first layer 190 of the balloon body 140. The balloon chamber 150 is in communication with the lumen 100 of the shaft 20 for inflating and deflating the balloon 30.

Also, the balloon 30 includes a plurality of longitudinally extending rib members 210 disposed between the outer surface of the first layer 190 and the inner surface of the second layer 200 of the balloon body 140, as shown in FIGS. 2 and 3. Preferably, the rib members 210 extend though the entire length of the balloon body 140 and are circumferentially disposed about the first layer 190 of the balloon body 140. The rib members 210 are preferably made from the same material as the two layers 190, 200 of the balloon body and preferably from a single piece of balloon material. Some exemplary materials that may be used to form the first and the second layers 190, 200 of the balloon body 140 were provided above. Preferably, the rib members are integral with the two layers of the balloon body and connect the two layers of the balloon body, as illustrated in FIG. 3.

The rib members 210 can vary in number, shape and size. In certain instances, the balloon 30 can include at least two rib members 210. In certain other embodiments, the balloon 30 can include at least three rib members 210. In certain other instances, the balloon 30 can include at least four rib members 210. In yet further instances, the balloon 30 can include at least five rib members 210. The number of the rib members 210 can range from 2 to 5.

Figure 4A:
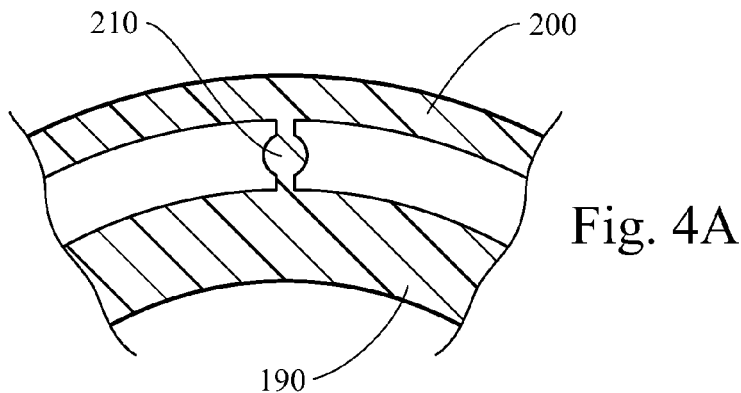
FIGS. 4A-4D depicts illustrative rib members.
Figure 4B:
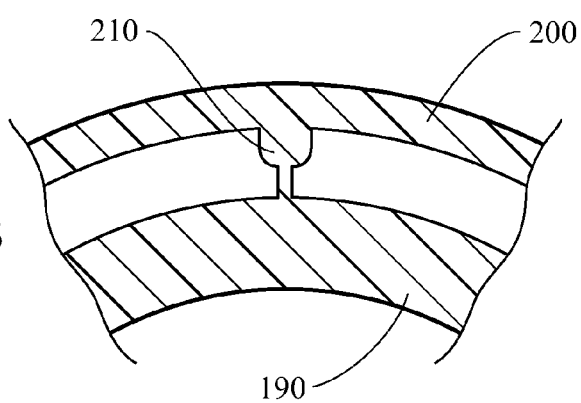
Figure 4C:
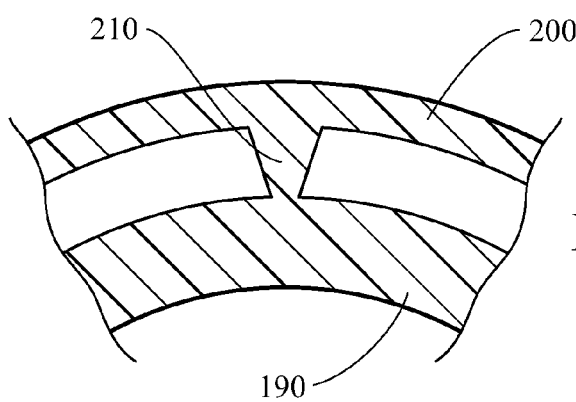
Figure 4D:
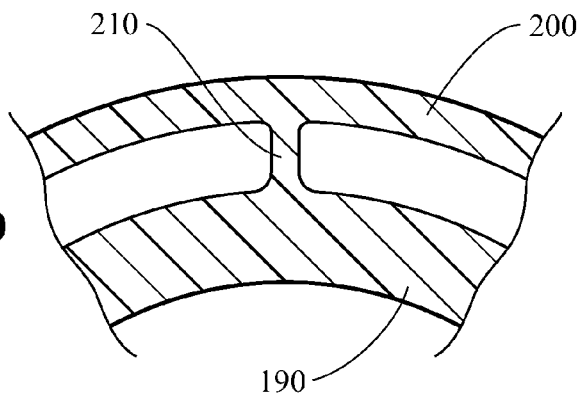

As illustrated in FIGS. 4A-4D, the rib members 210 can have various cross-sectional profiles or shapes. In cross section, the rib members may have a non-uniform or a substantially uniform configurations or profiles. For example, the rib members may have a substantially larger portion in the middle of the rib member (i.e., bulging in the middle, FIG. 4A); a substantially larger portion towards the second layer (i.e., outer wall) 200 (FIG. 4B); or a tapered profile though the first layer (i.e., inner wall) 190 (FIG. 4C). In other instances, the rib members may have a substantially uniform cross-sectional profile having a single dimension, as illustrated in FIG. 4D. Other cross-section profiles of the rib members 210 are also contemplated and may be suitable for use with the balloon catheter.

Concerning the size of rib members, the rib members may have height and width from about 0.03 millimeters to about 0.50 millimeters. Preferably, the height and width can range from about 0.05 millimeters to 0.40 millimeters.

Referring back to FIG. 3, the rib members 210 form a plurality of sealed cavities 220 between the first and the second layers 190, 200. The thickness of the cavities 220 may vary depending on the desired overall thickness of the balloon 30, thickness of the two layers 190, 200 that form the balloon body 140, and application. Other factors may also play a role. Specifically, the size of the rib members may play the key role for this, in that the cavity thickness will never be greater than the pre-molded rib height. Additionally, the thickness of the cavities may further depend on the blow molding method selected to form the balloon. The desired cavity thickness is preferably the same as the preferred rib heights (0.03 millimeters to 0.5 millimeters)

By including the rib members 210 within the double-walled balloon portion 30 of the dilation balloon catheter device 10, the balloon catheter 10 can be used for high pressure applications. The rib members 210 function to resist any tearing along the longitudinal pathway. The rib members 210 advantageously allow the two layers 190, 200 of the balloon body 140 to expand independently of each other during inflation of the balloon 30, while maintaining contact with each other. Because the layers 190, 200 are in contact with each other during inflation but moving independently, as discussed previously, the overall burst will be significantly higher than a single layer balloon having dimensions (e.g., thickness) equivalent to the dimensions of the two layers of the balloon body combined.

In addition, the rib members 210 function to resist circular tearing of the balloon under burst pressure.

In the embodiments heretofore described, a lubricant can be installed into the cavities 220 formed by the rib members. Preferably, the lubricant is installed into the cavities prior to blow molding. The lubricant in the cavities may enhance independent wall movements of the two layers of the balloon.

Some exemplary lubricants include, for example, silicone and glycerol. Other lubricants may also be used and are also contemplated.

In one alternative embodiment illustrated in FIGS. 5A-C, the shaft 510 can have a coaxial configuration, where wire-guided dilation balloon catheter 500 includes an inner shaft 520 coaxially disposed within the main shaft 510 to which the balloon portion 530 is attached. Cross-sectional views though B-B and C-C of the balloon catheter of FIG. 5A are shown in FIGS. 5B and 5C, respectively. The inner shaft 520 serves as the conduit for the wire guide 540, which in one embodiment, is a standard 0.035" wire guide that is loaded into, and is extendable from the inner shaft lumen 550. In the illustrative embodiment, both the inner and main shafts 520, 510 can be made of poly-ether ether ketone (PEEK). In other embodiments, a metal hypotube may be employed for all or at least the proximal portion 560 of the shaft 510. The inner and outer shafts 520, 510 are sized to allow the flow of inflation fluid within the annular space 570 between the two shafts 510, 520 and into the balloon chamber 580 of the balloon 530 to expand the balloon 530.

The inner shaft 520 can terminate within the distal end 590 of the balloon 530 or a few millimeters distally thereof. The wire guide 540 is typically utilized for adding stiffness or pushability to the balloon catheter 500, or it may be introduced separately into the patient and then used to guide the balloon catheter into the patient. The inner shaft 520 alone may provide sufficient stiffness and pushability for some applications. If desired, a wire guide 540 may at some point be replaced with a different wire guide having characteristics more desirable for a particular procedure. In the illustrative embodiment, the inner shaft 520 comprises a port 400 through a side wall thereof in communication with the wireguide lumen 550, the port being located proximal of the balloon 530 and a substantial distance from the proximal end 560 of the shaft 510. A standard hub 300 provides a port 310 for the infusion of a balloon inflation fluid, such as water or saline.

Alternatively, the outer and inner shafts may be fixed relative to one another longitudinally by a standard hub, which provides access for the wire guide, and a port for the infusion of a balloon inflation fluid, as described above in connection with a dual lumen shaft.

Method of Making the Device

Various methods may be utilized to form the balloon catheter described herein. One exemplary method of making multi-layered balloons is described in PCT Pub. No. WO 07/75585A2 and U.S. Pub. No. 2007/0167973A1, the entire contents of which are hereby incorporated by reference. Additionally, U.S. Provisional Pat. Application Ser. No. 61/036,176 filed Mar. 13, 2008 describes a process of making a balloon that may be suitable to form the inner and the outer layers of the balloon of the balloon catheter described herein.

Figure 7:
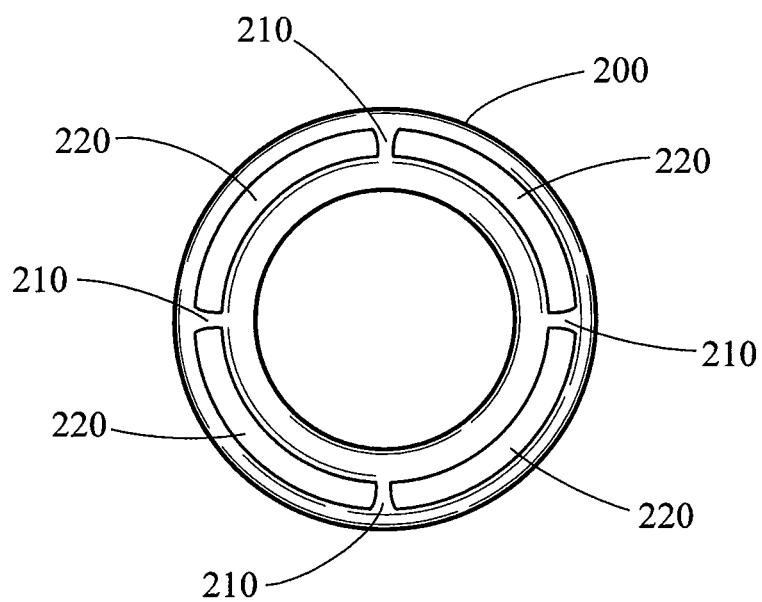
FIG. 7 depicts an exemplary shape of the extruded balloon material.

Specifically, the balloon can be made according to the following process. The balloon material is first extruded into a suitable shape, as seen for example in FIG. 7. The extruded balloon material is then placed into a forming mold to blow mold the balloon portion of the balloon catheter. Heat (above $T_g$ but below the melting temperature for the material) and low pressure (2-5 ATM) is applied. The cavities 220 are blocked, closed off or plugged prior to the balloon forming process/pressurization process. Only the inner lumen of the raw balloon material is pressurized (the cavities are not under pressure, as this would cause them to blow out). Next, the balloon material is stretched longitudinally, which will decrease the overall dimensions (or cross sectional area) of the balloon material, and give it the necessary longitudinal strength. Next, high pressure is applied to the mold to radially expand the balloon into the shape of the mold. This gives the balloon the necessary radial strength and shape. The ribs 210 prevent expansion of the second balloon layer 200, and thereby leaving a one-piece balloon with ribs. The ribs 210 run the entire length of the balloon, including the tapers (not shown in this figure).

In an exemplary method of using the balloon catheter device of the present invention, to dilate a stricture, a small incision is made in the patient to facilitate the insertion of a long, thin introducer sheath. A guide catheter is then passed through the sheath and into the narrowed artery. The physician may monitor the insertion of the guide catheter under fluoroscopy. An injection through the guide catheter of contrast dye/medium allows the physician visualization of the peripheral arteries.

Once the guide catheter is engaged in the ostium of the artery where the lesion/vessel stricture is located, a wire guide is threaded through the guide catheter. The wire guide is then advanced under fluoroscopy beyond the lesion to a distal location within the artery. With the wire guide in place, the dilation balloon catheter of the present invention is inserted over the wire guide and advanced to the lesion site, as illustrated in FIGS. 8 and 9.

Figure 8:
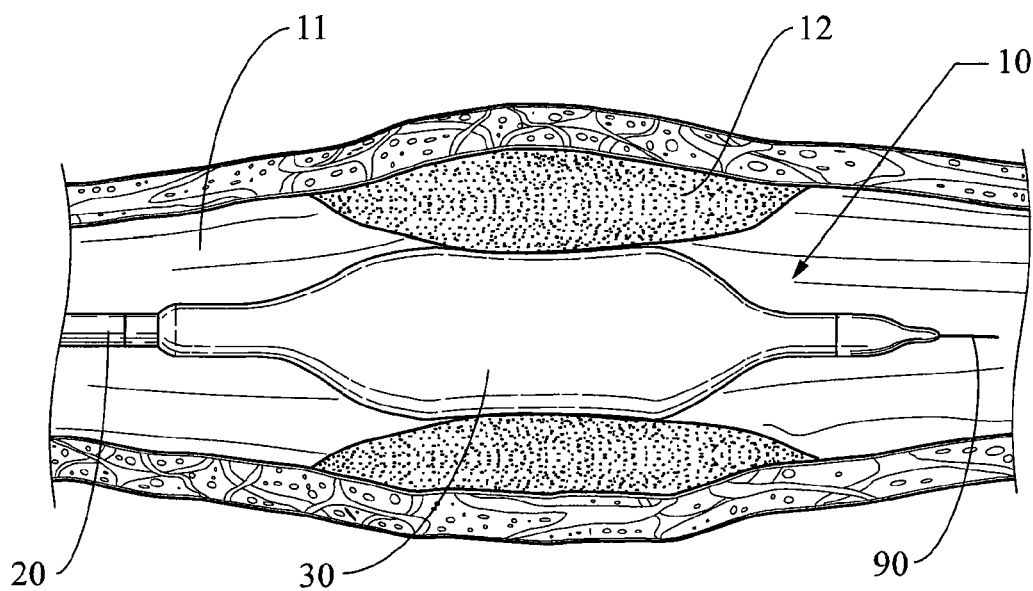
FIG. 8 depicts an exemplary dilation balloon catheter device deployed in a body lumen.

Referring to FIG. 8, once the balloon catheter 10 comprising a shaft 20 and a balloon 30, and optionally a wireguide 90, has been properly positioned in the bodily lumen 11, the balloon 30 is dilated within the artery at the lesion/stricture site 12, causing a compression of the arterial plaque against the inner lining of the arterial wall. Subsequent balloon dilation may be used if the physician decides to increase the atmospheres of pressure or duration of time that the balloon is applied to the lesion.

Figure 9:
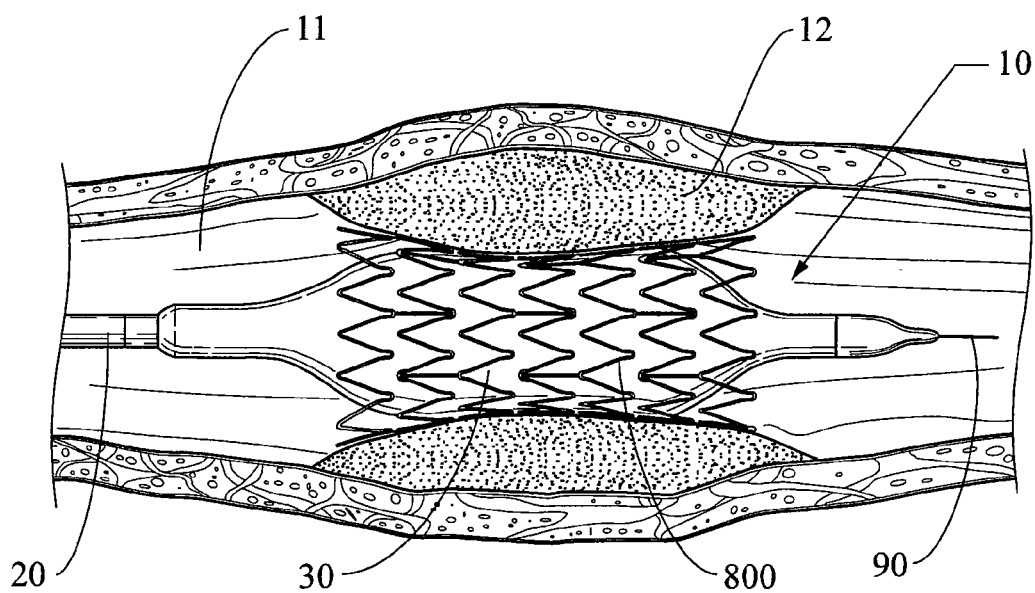
FIG. 9 depicts yet another embodiment of the exemplary dilation balloon catheter deployed in a body lumen.

Referring to FIG. 9, in addition or alternatively, the exemplary device of this invention may be used to expand and deploy a stent 800. Specifically, upon examination of the pre and post PTA images, the physician may decide to follow the PTA procedure with the implantation of a stent 800 at the site of the lesion. A stent 800 may be provided, which can then be compressed about the balloon 30 when the balloon is in an uninflated state. Once in position, the balloon can be expanded to expand and deploy the stent.

The physician may also consider using an adjunctive imaging device such as intravascular ultrasound (IVUS). This provides the physician with a cross-sectional and longitudinal image of the vessel and morphology of the plaque. IVUS allows for measurement of the artery and the plaque burden, which assists the physician with accurate sizing of the stent to be used.

It will be appreciated that the devices described herein will be useful in catheters, particularly high-pressure vascular balloon catheters, other types of medical procedures and in various types of balloons, wherein they will provide structural strength to resist bursting under pressure, torsional and longitudinal directivity and kink resistance while maintaining the small diametric profile necessary for traversing small tortuous vascular channels.

All patents, patent applications, provisional applications, and publications referred to or cited herein are incorporated by reference in their entirety, including all figures and tables, to the extent they are not inconsistent with the explicit teachings of this specification.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. A method of manufacture a dilation balloon catheter comprising:
    (i) extruding a single piece of a non-compliant raw balloon material into a tubular shape extending between a first end and a second end, the tubular shape comprising a first layer, a second layer, a plurality of longitudinally extending rib members between the first and the second layers and forming a plurality of cavities between the first and the second layers, the rib members having a non-uniform cross-sectional profile, and an inner lumen within the first layer;
    (ii) placing the extruded balloon material into a forming mold;
    (iii) blow molding the extruded balloon material into a balloon shape of the mold so as to form a balloon body having an outer balloon diameter, wherein only the inner lumen of the extruded balloon material is pressurized;
    (iv) disposing the balloon body on a portion of a distal end of a shaft.

2. The method of claim 1, further comprising clamping the first and the second ends of the extruded balloon material prior to the blow molding step.

3. The method of claim 1, wherein the step of blow molding comprises applying high pressure within the inner lumen of the extruded balloon material to radially expand the balloon body.

4. The method of claim 1, wherein the step of blow molding comprises applying high pressure within the inner lumen of the extruded balloon material to longitudinally stretch the balloon body.

5. The method of claim 1, wherein the step of blow molding comprises applying high pressure within the inner lumen of the extruded balloon material to radially expand and longitudinally stretch the balloon body.

6. The method of claim 1, wherein the step of blow molding comprises applying heat of above $T_g$ and pressure of about 2-5 ATM.

7. The method of claim 1, wherein the disposing step comprises attaching the balloon to the shaft.

8. The method of claim 7, wherein the attaching step comprises inserting a portion of the distal end of the shaft into a proximal opening of the balloon body and bonding thereto using an ultraviolet-curable adhesive or heat.

9. The method of claim 7, wherein the attaching step comprises the use of a solvent or glue.

10. The method of claim 1, wherein an inflated diameter of the first layer is slightly smaller than an inflated diameter of the second layer.

11. The method of claim 1, wherein the balloon material is selected from the group consisting of Nylon 12, poly(ethylene terephthalate, PEEK, PEBAX, or a block copolymer thereof.

12. The method of claim 1, wherein the balloon body has a burst pressure of at least 12 ATM.

13. The method of claim 1, wherein the thickness of the cavities of the balloon body is decreased as compared to a rib height before the blow molding step.

14. The method of claim 1, further comprising installing a lubricant into the cavities.

15. The method of claim 1, further comprising coaxially disposing an inner shaft within the portion of the shaft.

16. The method of claim 1, wherein the outer balloon diameter ranges from about 2 millimeters to about 30 millimeters.

17. The method of claim 1, wherein the balloon body ranges in length from about 2 centimeters to about 25 centimeters.

18. A dilation balloon catheter produced by the method of claim 1, wherein the dilation balloon catheter comprises
    a tubular shape extending between a first end and a second end, the tubular shape comprising
        a first layer,
        a second layer,
        a plurality of longitudinally extending rib members between the first and the second layers and forming a plurality of cavities between the first and the second layers, the rib members having a non-uniform cross-sectional profile, and
        an inner lumen within the first layer.

19. The method of claim 1, wherein the non-uniform cross-sectional profile is selected from at least one of the following cross-sectional profiles:
    (a) a substantially larger portion in the middle of the rib member;
    (b) a substantially larger portion towards the second layer; and
    (c) a tapered profile through the first layer.

20. The method of claim 1, wherein the balloon body has a burst pressure of at least 20 ATM.

21. The method of claim 1, wherein the balloon body has a burst pressure of at least 30 ATM.

* * * * *